United States Patent [19]
Blythin et al.

[11] 4,405,810
[45] Sep. 20, 1983

[54] 7-ARYL-HEPT-5-YNOIC ACIDS AND DERIVATIVES THEREOF

[75] Inventors: David Blythin, West Caldwell; Michael J. Green, Skillman, both of N.J.

[73] Assignee: Schering Corporation, Kenilworth, N.J.

[21] Appl. No.: 388,060

[22] Filed: Jun. 14, 1982

[51] Int. Cl.³ .............................................. C07C 63/64
[52] U.S. Cl. .................................... 562/495; 562/471; 562/490; 562/492; 560/59; 560/60; 560/100; 560/104; 260/501.1; 260/501.17; 424/308; 424/317
[58] Field of Search ............... 562/490, 492, 495, 471; 560/59, 60, 100, 104

[56] References Cited

U.S. PATENT DOCUMENTS 3,845,089 10/1974 Henrich ................................ 560/104
3,859,338 1/1975 Engel et al. ......................... 562/492
4,021,479 5/1977 Seeger .................................. 562/492

OTHER PUBLICATIONS

Doukas, H. M., J.O.C., vol. 19, No. 3, Mar. 1954, pp. 343-351.

Primary Examiner—Paul J. Killos
Attorney, Agent, or Firm—Stephen I. Miller; Bruce M. Eisen; Anita M. Magatti

[57] ABSTRACT

7-arylhept-5-ynoic acids and derivatives thereof are anti-allergy and anti-inflammatory agents. As such, they are useful in the treatment of allergy-caused diseases, particularly chronic obstructive lung diseases.

11 Claims, No Drawings

7-ARYL-HEPT-5-YNOIC ACIDS AND DERIVATIVES THEREOF

The present invention relates to a group of 7-aryl-hept-5-ynoic acids and derivatives thereof. More particularly, this invention relates to compounds having the general formula

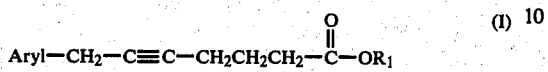

wherein Aryl is selected from the group consisting of

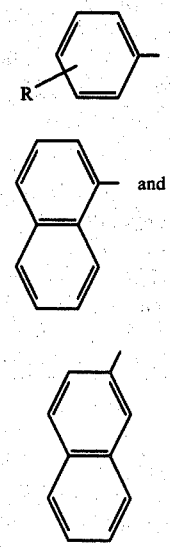

wherein R is hydrogen; phenyl; straight- or branched-chain alkyl containing from 1 to 12 carbon atoms; (cycloalkyl)alkyl containing from 3 to 12 carbon atoms; phenoxy; phenyl-$(CH_2)_m$— wherein m is 0, 1 or 2; $C_nH_{2n+1}$—O—$CH_2$— wherein n is 1-10; or $C_pH_{2p+1}$—O— wherein p is 1-12; $R_1$ is hydrogen, lower alkyl or phenyl; and the non-toxic pharmaceutically acceptable alkali metal, alkaline-earth metal, ethanolamine and N-methylglucamine salts thereof.

The straight- or branched-chain alkyl groups and the $C_pH_{2p+1}$ groups containing from 1 to 12 carbon atoms referred to above are exemplified by groups such as methyl, ethyl, n-propyl, n-butyl, n-pentyl, n-hexyl, n-heptyl, n-nonyl, n-decyl, n-undecyl, n-dodecyl, 3-methyloctyl, and 4-n-butylheptyl. The (cycloalkyl)alkyl groups contain from 3 to 12 carbon atoms and contain 3 to 7 carbon atoms in the ring portion. Examples are those such as cyclohexyl-methyl, cyclopentyl-n-butyl and the like. Similarly, the $C_nH_{2n+1}$ groups referred to above contain 1 to 10 carbon atoms and are those such as methyl, ethyl, n-propyl, n-butyl, n-pentyl, n-hexyl, n-heptyl, n-nonyl and n-decyl and the branched chain isomers thereof.

The lower alkyl groups referred to above contain from 1 to 6 carbon atoms and are exemplified by methyl, ethyl, propyl, butyl, pentyl, hexyl and the corresponding branched chain isomers thereof.

The non-toxic pharmaceutically acceptable salts of the compounds of formula I are the alkali metal, alkaline-earth metal, ethanolamine and N-methylglucamine salts thereof. Representative salts are the lithium, sodium, potassium, barium, strontium, calcium, ethanolamine and N-methylglucamine salts.

As indicated by the floating R group in formula I, the R substituent may be in the ortho, meta or para position of the phenyl ring.

Preferred compounds of this invention are those wherein $R_1$ is hydrogen. Also preferred are those wherein Aryl is a group of the formula

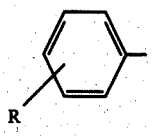

wherein R is as hereinbefore defined.

The compounds wherein R is a hydrogen, p-phenyl, p-undecyloxy, p-(n-octyl)- or a p-(n-undecyloxymethyl)group are also especially preferred. Also preferred are the calcium and sodium salts of these compounds.

The compounds of this invention are useful by reason of their valuable biological properties. In particular, they possess anti-allergy and anti-inflammatory activity. Thus, they are useful for treating chronic obstructive lung diseases such as asthma, bronchitis and the like. These chronic obstructive lung diseases can result from allergic reactions or have non-allergic causes. The compounds of this invention can thus be used to treat allergy caused diseases and their preferred use is for treating allergic chronic obstructive lung diseases. Chronic obstructive lung disease as used herein means those disease conditions in which the passage of air through the lungs is obstructed, or diminished, such as is the case with asthma, bronchitis and the like.

The anti-allergy activity of the active compounds of this invention may be identified by tests which measure its inhibition of anaphylactic bronchospasm in sensitized guinea pigs challenged with aerosolized antigen. The animals are treated with propranolol, mepyramine and indomethacin, thereby excluding released histamine and prostaglandins/thromboxanes as the cause of the bronchospasm.

This process of elimination indicates that a good part of the bronchospasm is due to SRS-A which is likely to be susceptible to inhibition by SRS-A synthesis/release inhibitors and receptor antagonists. Compounds are tested in both oral and parenteral administrations.

The anti-allergy dose of a compound of this invention varies according to its route of administration. The compounds of this invention, when administered orally, are active at dosages of from about 1 to 100 mg/kg of body weight; when administered parenterally, e.g., intravenously, the compounds exhibit activity at dosages of from about 0.1 to 10 mg/kg body weight. Inhalation doses are from about 0.01 to 1 mg/kg body weight.

The required daily dosage may be administered in single or divided doses. The exact dose to be administered will, of course, be dependent upon various factors such as the particular compound employed, age and weight of the subject mammel and the individual patients response. A typical recommended dosage regimen is oral administration of from 20 to 1500 mg/day, preferably 500 to 800 mg/day, in two to four divided doses to achieve relief of the allergic symptoms.

The compounds of the present invention can be administered orally, parenterally or by inhalation. Preferably, and most advantageously, the mode of administration is oral. The compounds may be combined with any suitable pharmaceutical carrier and administered in a variety of formulations. Typical oral formulations are those such as tablets, solutions and suspensions. Inhalation formulations are typically solutions, nasal sprays, aerosolized sprays, or lung inhalant sprays.

Typical acceptable pharmaceutical carriers for use in formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinylpyrrolidone; polyvinyl alcohol; stearic acid; alkaline earth metal stearates such as magnesium stearate and calcium stearate; stearic acid vegetable oils, sesame oil, olive oil and corn oil; non-ionic, cationic and anionic surfactants; ethylene glycol polymers; beta-cyclodextrin; fatty alcohols; hydrolyzed cereal solids; petrolatum, sterilized water; as well as other non-toxic compatible fillers, binders, disintegrants and lubricants commonly used in pharmaceutical formulations.

The compounds of formula I wherein $R_1$ is hydrogen are conveniently prepared by reaction of an aryl bromide of the formula II

Aryl—CH$_2$—BR  (II)

wherein Aryl is as hereinbefore defined with hex-5-ynoic acid which has previously been treated with sodium hydride. Typically, this reaction is conducted in an organic solvent such as dimethylformamide at temperatures ranging from about 50°–100° C.

This method is useful for the preparation of the following compounds:

7-phenylhept-5-ynoic acid;
7-(1-naphthyl)hept-5-ynoic acid; and
7-(2-naphthyl)hept-5-ynoic acid.

Another method of preparation for the compounds of formula I wherein $R_1$ is hydrogen involves the reaction of hex-5-ynoic acid with ethylmagnesium bromide to form the intermediate of formula III

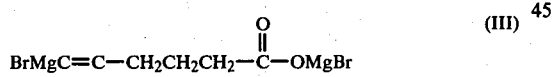

BrMgC≡C—CH$_2$CH$_2$CH$_2$—C(=O)—OMgBr  (III)

which is then reacted with the aryl bromide of formula II in the presence of CuCN to give the compound of formula I wherein $R_1$ is hydrogen.

This reaction is generally performed in an anhydrous solvent such as tetrahydrofuran or ethyl ether. The reaction to form the intermediate of formula III is generally carried out at a temperature of from about 0°–20° C., while the reaction of the intermediate of formula III with the aryl bromide of formula II is generally carried out at a temperature of 10°–50° C., with room temperature being generally preferred.

This reaction sequence can be utilized to prepare such examples of this invention as follows:

7-phenylhept-5-ynoic acid;
7-(4-biphenyl)hept-5-ynoic acid;
7-[p-(n-butyl)phenyl]-hept-5-ynoic acid;
7-[p-(n-pentyl)phenyl]hept-5-ynoic acid;
7-[p-(n-hexyl)phenyl]hept-5-ynoic acid;
7-[p-(n-heptyl)phenyl]hept-5-ynoic acid;
7-[p-(n-octyl)phenyl]hept-5-ynoic acid;
7-[p-(n-nonyl)phenyl]hept-5-ynoic acid;
7-[p-(n-decyl)phenyl]hept-5-ynoic acid;
7-[p-(n-undecyl)phenyl]hept-5-ynoic acid;
7-[p-(n-dodecyl)phenyl]hept-5-ynoic acid;
7-(1-naphthyl)hept-5-ynoic acid;
7-[p-(n-undecyloxy)phenyl]hept-5-ynoic acid; and
7-[p-(n-undecyloxymethyl)phenyl]hept-5-ynoic acid.

A further method of preparation for the compounds of formula I wherein $R_1$ is hydrogen involves the reaction of an aryl aldehyde of the formula IV

Aryl—CHO  (IV)

wherein Aryl is as hereinbefore defined, first with methoxymethyltriphenyl phosphonium chloride which had previously been treated with phenyllithium and then with a strong aqueous organic acid, e.g., methanolic hydrochloric acid, to afford the aldehyde of the formula V

Aryl—CH$_2$—CHO  (V)

wherein Aryl is as hereinbefore defined.

This aldehyde of formula V is then treated first with a combination of carbon tetrabromide, triphenylphosphine and zinc dust and then with n-butyllithium (according to the method of Corey and Fuchs, *Tet. Letters,* 1972, 3769-72) to yield the acetylene of formula VI

Aryl—CH$_2$C≡CH  (VI)

wherein Aryl is as hereinbefore defined. Alternately, the aldehyde of formula V can be treated first with chloromethyltriphenylphosphine chloride which had previously been treated with n-butyllithium (according to the method of Corey and Ruden, *Tet. Letters,* 1973, 1495-9) to afford the acetylene of formula VI.

The acetylene of formula VI is then reacted with a chloro or bromo acid of the formula VII

$$X-CH_2CH_2CH_2\overset{O}{\overset{\|}{C}}-OH \qquad (VII)$$

wherein X is chloro or bromo, in liquid ammonia in the presence of lithium amide to afford the compound of formula I wherein $R_1$ is hydrogen.

Alternatively, the acetylene of formula VI may be reacted under similar conditions with a chloro or bromo alcohol of the formula VIII

X—CH$_2$CH$_2$CH$_2$CH$_2$—OH  (VIII)

wherein X is chloro or bromo, to afford an alcohol of formula X

Aryl—CH$_2$—C≡C—CH$_2$CH$_2$CH$_2$CH$_2$OH  (IX).

Oxidation of this alcohol of formula IX with pyridinium dichromate in dimethyl formamide affords the desired compound of formula I.

An alternate process for the preparation of the compounds of formula I wherein $R_1$ is hydrogen or lower alkyl involves reaction of a compound of the formula X

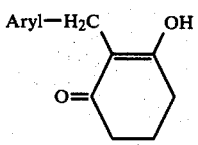

wherein Aryl is as hereinbefore defined with hydrazinetosylate of the formula XI

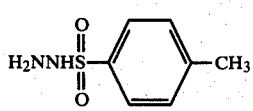

to afford the tosylhydrazone of the formula XII. This reaction is preferably conducted in solvent such as methanol, in the presence of an acid, for instance, hydrochloric acid. Typical temperatures range from 0°–50° C., with room temperature being generally satisfactory. Typical reaction times range from about 1 to 5 hours.

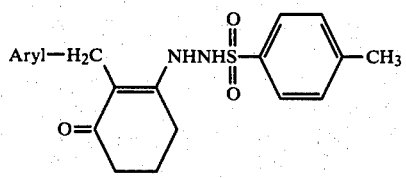

The tosylhydrazone of formula XII is then oxidized, utilizing a strong oxidizing agent such as periodic acid, to afford the compound of formula XIII

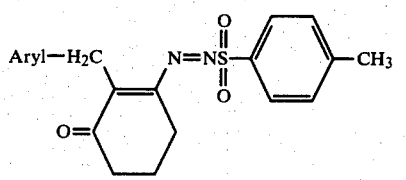

This reaction is preferably conducted in the same reaction medium as the previous step, except that lower temperatures, ranging from about −20° to 0° C., are utilized.

The compound of formula XIII is then treated with a sodium alkoxide to afford a compound of formula I wherein $R_1$ is lower alkyl. Typically, the same reaction medium is utilized as previously. Typical times range from about 1 to 5 hours, while typical reaction temperatures range from about 0°–100° C., with 20°–65° C. being generally satisfactory. This compound of formula I wherein $R_1$ is lower alkyl is then saponified in a known manner to afford a compound of formula I wherein $R_1$ is hydrogen. Alternately, the compound of formula XIII may be treated with water and a suitable hydroxide, such as sodium or potassium hydroxide, to directly afford a compound of formula I wherein $R_1$ is hydrogen.

The above described reaction utilizing the tosylhydrazone intermediate can be utilized for the preparation of such examples of this invention as follows:

methyl 7-phenylhept-5-ynoate;
7-phenylhept-5-ynoic acid;
ethyl 7-phenylhept-5-ynoate;
7-(1-naphthyl)hept-5-ynoic acid;
methyl 7-(1-naphthyl)hept-5-ynoate;
7-[p-(n-octyl)phenyl]hept-5-ynoic acid; and
methyl 7-[p-(n-octyl)phenyl]hept-5-ynoate.

The compounds of formula I wherein $R_1$ is lower alkyl or phenyl may be produced by esterification methods well-known in the chemical arts. For instance, where the methyl ester ($R_1$=methyl) is desired, treatment of the acid ($R_1$=hydrogen) with diazomethane in ethyl ether results in the desired product.

The alkali metal salts of the compounds of formula I can be readily prepared by reacting the free acid ($R_1$=hydrogen) with the appropriate alkali metal hydroxide solution. For instance, the sodium salt is prepared by reaction of the free acid with sodium hydroxide solution.

Alternately, the compounds of formula I wherein $R_1$ is sodium can be prepared by reaction of a compound of formula II with a disodium salt of the formula XIV

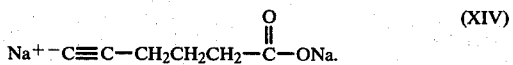

This disodium salt of formula XIV is prepared by treatment of methyl hex-5-ynoate first with sodium hydroxide followed by elemental sodium in liquid ammonia.

The alkaline earth metal salts of the compounds of formula I can be prepared by reaction of the sodium salt of formula I with an alkaline earth metal chloride. For instance, the calcium salt is preparable by reaction of the sodium salt with calcium chloride.

The amine salts can be prepared from the free acid ($R_1$=hydrogen) by contacting it with the appropriate amine in a compatible organic solvent.

The following examples describe in detail compounds and pharmaceutical compositions illustrative of the present invention and methods which have been devised for their preparation. It will be apparent to those skilled in the art that many modifications, both of materials and methods, may be practiced without departing from the purpose and intent of this disclosure.

EXAMPLE 1

7-Phenylhept-5-ynoic acid, and Sodium and Calcium salts

A solution of hex-5-ynoic acid (1 mmole) in dimethylformamide (50 ml) is treated with sodium hydride (2 mmole; 50% dispersion in oil) first at room temperature, then at 60° C. A copious evolution of hydrogen occurs. Then, the solution is cooled and benzyl bromide (1.5 mmole) is added. The reaction mixture is heated to 80° C. and maintained thereat until then layer chromatography indicates the consumption of all the hex-5-ynoic acid. After cooling, the solution is poured onto a 10% sodium hydroxide solution and extracted with ethyl ether to remove unreacted benzyl bromide. The aqueous layer is then acidified to pH2 with concentrated hydrochloric acid, and extracted with chloroform. Removal of the solvent from the chloroform layer affords a residue which is distilled under reduced pressure to give the desired title product, 7-phenylhept-5-ynoic acid.

Treatment of 7-phenylhept-5-ynoic acid with sodium hydroxide solution gives sodium 7-phenylhept-5-nyoate.

Treatment of sodium 7-phenylhept-5-ynoate with calcium chloride affords calcium 7-phenylhept-5-ynoate.

EXAMPLE 2

7-Phenylhept-5-ynoic acid

Hex-5-ynoic acid (0.1 mole) is added to a tetrahydrofuran solution of ethylmagnesium bromide (0.2 mole) maintained at 5° C. When the addition is complete, the solution is warmed to room temperature and CuCN (0.5 g) is added with stirring. After 20 minutes, a solution of benzylbromide (0.05 mole) in tetrahydrofuran is added dropwise over a one-half hour period. The reaction is maintained at room temperature until thin layer chromatography shows completion and then poured onto 1 N hydrochloric acid. This mixture is then extracted with ethyl ether and the ether layer separated. Removal of the ether gives a residue which is distilled under reduced pressure to afford the title product, 7-phenylhept-5-ynoic acid.

EXAMPLE 3

7-[p-(n-undecyloxymethyl)phenyl]hept-5-ynoic acid

Repetition of the procedure detailed in Example 2 utilizing p-(n-undecyloxymethyl)benzyl bromide in place of the benzyl bromide affords the title compound, 7-[p-(n-undecyloxymethyl)phenyl]hept-5-ynoic acid.

EXAMPLE 4

7-[p-(n-octyl)phenyl]hept-5-ynoic acid

Utilizing p-(n-octyl)benzyl bromide in place of the benzyl bromide of Example 2 and substantially repeating the procedure detailed therein affords the title compound, 7-[p-(n-octyl)phenyl]hept-5-ynoic acid.

EXAMPLE 5

7-[p-(n-undecyloxyl)phenyl]hept-5-ynoic acid

Substantially repeating the procedures detailed in Example 2 utilizing p-(n-undecyloxy)benzyl bromide in place of the benzyl bromide affords the title compound, 7-[p-(n-undecyloxy)phenyl]hept-5-ynoic acid.

EXAMPLE 6

7-[p-(n-octyl)phenyl]hept-5-ynoic acid

A. Methoxymethyltriphenylphosphonium chloride (0.06 mole) in ethyl ether is treated with phenyllithium (0.06 mole) at room temperature. This reaction mixture is cooled to −40° C. and to this is added p-(n-octyl)benzaldehyde (0.06 mole). The resulting mixture is allowed to come to room temperature. When thin layer chromatography shows completion of the reaction, the mixture is filtered. The filtrate is washed first with dilute hydrochloric acid, then with water, dried, and evaporated to give as a residue, the methoxyl methylene adduct of p-(n-octyl)benzaldehyde.

This product is taken up into an aqueous methanolic hydrochloric acid solution. After standing at room temperature, the solution is neutralized with sodium hydroxide and then extracted with methylene chloride. After separation, the methylene chloride is removed by evaporation to give a residue which is distilled under reduced pressure to afford p-(n-octyl)phenylacetaldehyde.

B. p-(n-Octyl)phenylacetaldehyde (1 mmole, prepared as described in paragraph A of this example) is dissolved in methylene chloride, and treated with carbontetrabromide (4 mmole), triphenylphosphine (4 mmole) and zinc dust (4 mmole) at room temperature. The reaction mixture is then diluted with ethyl ether and filtered. The filtrate is washed with water, dried and evaporated to give an oily residue. This residue is dissolved in tetrahydrofuran and treated with n-butyl lithium (2.1 mmole) at −78° C. for one hour and then at room temperature until the reaction ceases. The reaction mixture is poured onto water, the pH adjusted to 7, and extracted with methylene chloride. The methylene chloride extract is washed with water, dried and the solvent removed by evaporation. Distillation under reduced pressure affords p-(n-octyl)benzylacetylene.

C. A solution of lithium amide in liquid ammonia is prepared by the addition of lithium metal (2 mmoles) to liquid ammonia containing a trace amount of ferrous sulfate. To this solution is added 4-chlorobutyric acid (1 mmole) and p-(n-octyl)benzylacetylene (1 mmole, prepared as described in paragraph B of this example). After a suitable time at refluxing liquid ammonia temperatures, the ammonia is removed by evaporation and the residue dissolved in 10% sodium hydroxide solution. After extraction with ether, the aqueous layer is acidified to a pH of 2–3 with concentrated hydrochloric acid, and extracted with methylene chloride. The methylene chloride layer is separated and the solvent removed by evaporation to give a residue. This residue is purified either by column chromatography or molecular distillation under reduced pressure to afford the desired title product, 7-[p-(n-octyl)phenyl]hept-5-ynoic acid.

EXAMPLE 7

7-[p-(n-octyl)phenyl]hept-5-ynoic acid

A. n-Butyllithium (1.85 mmole) is added to a cooled (−78° C.) suspension of chloromethyltriphenyl phosphine chloride (1.85 mmole) in tetraydrofuran. After one hour, p-(n-octyl) phenylacetaldehyde (1.2 mmole, prepared as detailed in paragraph A of example 6) is added and the temperature raised to 0° C. When all the aldehyde is consumed, the reaction mixture is extracted with hexane and the hexane extract filtered through a short column of acidic alumina. Evaporation of the solvent gives the chloro-olefin, which is dissolved in tetrahydrofuran, cooled to 0° C., and treated with excess n-butyllithium. When the reaction ceases, the reaction mixture is poured onto water, brought to neutral pH and extracted with methylene chloride. The methylene chloride extract is washed with water, dried and the solvent removed by evaporation. Distillation under reduced pressure affords p-(n-octyl)benzylacetylene.

B. A solution of lithium amide in liquid ammonia is prepared by the addition of lithium metal (2 mmoles) to liquid ammonia containing a trace amount of ferrous sulfate. To this solution is added 4-bromo-n-butanol (1 mmole) and p-(n-octyl)benzylacetylene (1 mmole, prepared as described in paragraph B of Example 6 or in paragraph A of this example). After a suitable time at refluxing liquid ammonia temperatures, the ammonia is removed by evaporation and the residue dissolved in water. After extraction with chloroform, the chloroform layer is separated and the solvent removed by evaporation to give a residue. This residue is purified by distillation under vacuum to give 7-[p-(n-octyl)phenyl]-5-heptyn-1-ol.

C. 7-[p-(n-octyl)phenyl]-5-heptyn-1-ol (1.7 mmole) is dissolved in dimethyl formamide and to the resulting solution is added, with stirring, pyridinium dichromate (11.7 mmoles). After stirring for 48 hours at room temperature, the reaction mixture is poured onto a 10% sodium hydroxide solution and extracted with ethyl ether. The aqueous layer is acidified to pH of 2-3 with concentrated hydrochloric acid and extracted with chloroform. The chloroform layer is separated, the solvents removed by evaporation and the residue distilled under reduced pressure to afford the title compound, 7-[p-(n-octyl)phenyl]hept-5-ynoic acid.

EXAMPLE 8

7-[p-(n-Undecyloxymethyl)phenyl]hept-5-ynoic acid

A. 1,4-Benzenedimethanol (1.5 moles) in dimethylformamide is treated with sodium hydride (0.75 mole) at 40° C. When hydrogen evolution ceases, n-undecylbromide (0.75 mole) is added and the reaction heated to 80° C. for 24 hours. Distillation under reduced pressures removes, in order, dimethylformamide, unreacted 1,4-benzenedimethanol, and finally p-(n-undecyloxymethyl)benzyl alcohol.

B. p-(n-Undecyloxymethyl)benzyl alcohol (10 mmoles) is dissolved in methylene chloride and treated with pyridinium chlorochromate (12 mmoles) at room temperature. When the reaction ceases, the reaction mixture is filtered through a pad of silica gel. The solvent is evaporated from this filtrate to afford the product, p-(n-undecyloxymethyl)benzaldehyde.

C. Following the procedure of paragraphs A-C of Example 6 utilizing p-(n-undecyloxymethyl)benzaldehyde in place of the p-(n-octyl)benzaldehyde used therein, affords the title product, 7-[p-(n-undecyloxymethyl)phenyl]hept-5-ynoic acid.

EXAMPLE 9

Methyl 7-phenyl-hept-5-ynoate

A. 1-benzyl cyclohexane-2,6-dione (17.25 g), p-toluenesulfonylhydrazine (16.52 g) in methanol (290 ml) was treated with concentrated HCl (1 ml) and left at room temperature for 48 hours. Evaporation of the solvent under reduced pressure and crystallization of the residue gave 1-benzylcyclohexane-2,6-dione mono-p-toluenesulfonylhydrazone (5 g) m.p. 172°-3° C.

B. The product of part A (3.9 g) in methanol (40 ml) was cooled to −5° C. and an aqueous solution of periodic acid (4.95 g in 6.5 ml of water) was added dropwise keeping the temperature at −5° C. After 1 hour at −5° C. the resulting orange crystals of 2-benzyl-1-p-toluenesulfonylazo-1-cyclohexen-3-one were filtered off and air dried (3.1 g) m.p. 80°-91° C.

C. The product of part B (3 g) in methanol (50 ml) is treated with NaOCH$_3$ (0.46 g) and the mixture heated under reflux for ½ hour. After evaporation of the methanol, the residue is dissolved in ether, washed with water, dried and the product distilled to give methyl-7-phenyl-hept-5-ynoate.

The following formulations exemplify some of the dosage forms in which the compounds of this invention may be employed.

EXAMPLE 10

| Ingredients | Tablets mg/tablet | mg/tablet |
|---|---|---|
| 7-[p-(n-octyl)phenyl]hept-5-ynoic acid | 100 | 500 |
| Lactose, USP | 122 | 113 |
| Corn Starch, Food Grade, as a 10% paste in purified water | 30 | 40 |
| Corn Starch, Food Grade | 45 | 40 |
| Magnesium Stearate, NF | 3 | 7 |
| | 300 | 700 |

Mix the active ingredient with the lactose for 10-15 minutes. Granulate with the 10% corn starch pase. Mill the damp granules through a course screen, if needed. Dry the damp granules, screen the dried granules, if needed, and mix with the corn starch. Add the magnesium stearate and mix for 1-3 minutes. Compress the mixture to appropriate size and weight on a suitable tablet machine.

EXAMPLE 11

| Ingredients | Capsules mg/tablet | mg/tablet |
|---|---|---|
| 7-[p-(n-octyl)phenyl]hept-5-ynoic | 100 | 500 |
| Lactose, USP | 106 | 123 |
| Corn Starch, Food Grade | 40 | 70 |
| Magnesium, NF | 4 | 7 |
| | 250 | 700 |

Mix the first three ingredients in a suitable blender for 10-15 minutes. Add the magnesium stearate and mix for 1-3 minutes. Fill the mixture into a suitable two-piece hard gelatin capsule on a suitable encapsulating machine.

EXAMPLE 12

| Parenteral Formulation Ingredients | mg/vial | mg/vial |
|---|---|---|
| 7-[p-(n-octyl)phenyl]-hept-5-ynoic acid sterile | 100 | 500 |

Add sterile water for injection or bacteriostatic water for injection for reconstitution.

EXAMPLE 13

| Injectable Formulation | mg/vial | mg/vial |
|---|---|---|
| 7-[p-(n-octyl)phenyl]hept-5-ynoic acid | 100 | 500 |
| Methylparaben | 1.8 | 1.8 |
| Propylparaben | 0.2 | 0.2 |
| Sodium Bisulfate | 3.2 | 3.2 |
| Dissodium Edetate | 0.1 | 0.1 |
| Sodium Sulfate | 2.6 | 2.6 |
| Water for injection to make. | 1.0 ml. | 1.0 ml. |

Dissolve the parabens in about 85% of the final volume of the water for injection at 65°-70° C. Cool to 25°-35° C. Charge and dissolve the sodium bisulfate, dissodium edetate and sodium sulfate. Charge and dissolve the active ingredient. Bring the solution to final volume by adding water for injection. Filter the solution through 0.22 membrane and fill into appropriate containers.

EXAMPLE 14

| Nasal Spray | |
|---|---|
| Ingredients | mg/vial |
| 7-[p-(n-octyl)phenyl]hept-5-ynoic acid | 10.0 |
| Phenyl Mercuric Acetate | 0.02 |
| Aminoacetic Acid USP | 3.7 |
| Sorbitol Solution | 57.0 |
| Benzalkonium Chloride Solution | 0.2 |
| Sodium Hydroxide Solution 1N (to adjust pH) | — |
| Water Purified USP to make | 1.0 ml |

Mix first five ingredients. Adjust pH using sodium hydroxide. Add purified water q.s. 1.0 ml.

EXAMPLE 15

| Lung Inhaler | |
|---|---|
| Ingredient | mg/container |
| 7-[p-(n-octyl)phenyl]-hept-5-ynoic acid | 10.0 |
| Oleic Acid | 1.0 |
| Fluorotrichloromethane | 4,739.0 |
| Dichlorodifluoromethane | 12,250.0 |
| | to make 17.000.0 |

Add oleic acid to previously cooled fluorotrichloromethane and mix with a high sheer mixer. While mixing, add the required amount of active ingredient and continue mixing until homogeneous. If necessary, adjust the suspension to the required weight with fluorotrichloromethane. Meter the required amount of suspension into each can. Crimp the valves onto the can. Pressure fill through valve required amount of dichlorodifluoromethane.

In each of the above Examples 10–15, 7-[p-(n-octyl)-phenyl]hept-5-ynoic acid can be replaced by an equally effective amount of 7-phenylhept-5-ynoic acid; 7-[p-(n-nonyl)phenyl]hept-5-ynoic acid; 7-[p-(n-decyl)phenyl]-hept-5-ynoic acid; 7-[p-(n-undecyloxy)phenyl]hept-5-ynoic acid, 7-[p-(n-undecyloxymethyl)phenyl]hept-5-ynoic acid, or any of the other compounds defined by formula I.

What is claimed is:

1. A compound of the formula

wherein Aryl is selected from the group consisting of

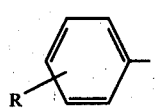

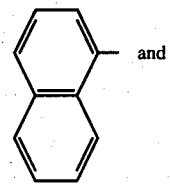 and

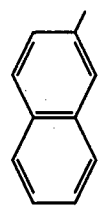

wherein
R is hydrogen; phenyl; straight- or branched-chain alkyl containing from 1 to 12 carbon atoms; (cycloalkyl)alkyl containing from 3 to 12 carbon atoms; phenoxy; phenyl$(CH_2)_m$—wherein m is 0,1 or 2;
$C_nH_{2n+1}$—O—$CH_2$—wherein n is 1–10; or
$C_pH_{2p+1}$—O— wherein p is 1–12;
$R_1$ is hydrogen, lower alkyl or phenyl; and the nontoxic pharmaceutically acceptable alkali metal, alkalineearth metal, ethanolamine and N-methylglucamine salts thereof.

2. A compound according to claim 1 wherein $R_1$ is hydrogen.

3. A compound according to claim 1 or 2 wherein Aryl is a group of the formula

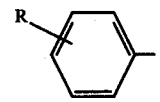

wherein R is hydrogen; phenyl; straight- or branched-chain alkyl containing from 1 to 12 atoms; (cycloalkyl)alkyl containing from 3 to 12 carbon atoms; phenoxy; phenyl $(CH_2)$—$_m$ wherein m is 0, 1 or 2; $C_nH_{2n+1}$—O—$CH_2$— wherein n is 1–10; or $C_pH_{2p+1}$—O— wherein $p$ is 1–12.

4. The compound according to claim 1 which is 7-phenyl-hept-5-ynoic acid.

5. The compound according to claim 1 which is 7-[p-(n-octyl)phenyl]hept-5-ynoic acid.

6. The compound according to claim 1 which is 7-[p-(n-undecyloxy)phenyl]hept-5-ynoic acid.

7. The compound according to claim 1 which is 7-[p-(n-undecyloxymethyl)phenyl]hept-5-ynoic acid.

8. The compound according to claim 1 which is 7-(4-biphenyl)hept-5-ynoic acid.

9. The compound according to claim 1 which is 7-(2-naphthyl)hept-5-ynoic acid.

10. A pharmaceutical composition adapted for the treatment of allergy-caused diseases which comprises an anti-allergy effective amount of a compound according to claim 1 in admixture with a pharmaceutically acceptable carrier therefor.

11. A method of treatment for allergy-caused diseases which comprises administering to an allergic mammal an anti-allergy amount of a compound according to claim 1.

* * * * *